United States Patent
Kidwell

(10) Patent No.: US 7,618,523 B2
(45) Date of Patent: *Nov. 17, 2009

(54) CAST MEMBRANE REFERENCE ELECTRODE AND METHOD OF MAKING

(75) Inventor: David A. Kidwell, Alexandria, VA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 980 days.

This patent is subject to a terminal disclaimer.

(21) Appl. No.: 10/833,636

(22) Filed: Apr. 26, 2004

(65) Prior Publication Data

US 2004/0217017 A1    Nov. 4, 2004

Related U.S. Application Data

(63) Continuation of application No. 10/237,074, filed on Sep. 9, 2002, now Pat. No. 6,780,307.

(60) Provisional application No. 60/328,423, filed on Oct. 12, 2001.

(51) Int. Cl.
*G01N 27/30*    (2006.01)
(52) U.S. Cl. ..................... 204/435; 427/2.13
(58) Field of Classification Search ................. 204/435; 427/2.11–2.13
See application file for complete search history.

(56) References Cited

U.S. PATENT DOCUMENTS

| 4,399,002 A | | 8/1983 | Freiser et al. |
|---|---|---|---|
| 4,454,007 A | | 6/1984 | Pace |
| 4,713,165 A | | 12/1987 | Conover et al. |
| 4,773,969 A | | 9/1988 | Miura |
| 4,891,125 A | * | 1/1990 | Schultz ................. 204/435 |
| 4,913,793 A | * | 4/1990 | Leonard ................. 204/433 |
| 5,180,481 A | | 1/1993 | Carey |

(Continued)

FOREIGN PATENT DOCUMENTS

JP    01-292246 A   *   11/1989

OTHER PUBLICATIONS

Derwent abstract of and figure from Schreurs et al. NL 8602668A, May 16, 1988.*

(Continued)

*Primary Examiner*—Alex Noguerola
(74) *Attorney, Agent, or Firm*—John J. Karasek; Stephen T. Hunnius

(57) ABSTRACT

A hand-held portable drug monitoring system to detect and quantitate cocaine and other organic drugs in saliva, sweat, and surface wipes by using an ion selective electrode or an array of ion selective electrodes. The ion selective electrode has a cast membrane reference electrode and a sensing electrode with a hydrophobic polymer, a plasticizer, and an ionophore selective for the organic drug to be tested. The ion selective electrode can be connected to a converter that coverts a voltage reading from the ion selective electrode to a quantitative drug concentration level. Also disclosed is the related method of using an ion selective electrode to detect an organic drug in saliva, sweat, and surface wipes, the method of testing electrical contact in an ion selective electrode, and the method of making a cast membrane reference electrode.

4 Claims, 8 Drawing Sheets

U.S. PATENT DOCUMENTS

| | | | |
|---|---|---|---|
| 5,522,978 | A | 6/1996 | Pace et al. |
| 5,531,870 | A | 7/1996 | Cha |
| 5,554,339 | A | 9/1996 | Cozzette et al. |
| 5,753,519 | A | 5/1998 | Durst et al. |
| 5,891,649 | A | 4/1999 | Kidwell et al. |
| 5,914,271 | A | 6/1999 | Law et al. |
| 6,033,914 | A | 3/2000 | Boyd et al. |
| 6,087,182 | A | 7/2000 | Jeng et al. |
| 6,165,796 | A | 12/2000 | Bell |
| 6,212,418 | B1 | 4/2001 | Even-Tov et al. |
| 2002/0065332 | A1 | 5/2002 | Choi |
| 2002/0130069 | A1 | 9/2002 | Moskoff |
| 2003/0176933 | A1 | 9/2003 | Lebel |

OTHER PUBLICATIONS

JPO abstract of Kamahori et al. Pat-No. JP 401292246 A, Nov. 24, 1989.*

Derwent abstract of Kamahori et al. Pub-No. JP 01292246 A, Nov. 24, 1989.*

English language translation of JP 01292246, patent published on Nov. 24, 1989.*

English language translation of NL 8602668, patent published May 16, 1988.*

Eman M. Elnemma & Marawan A. Hamada, "Liquid and Poly (Vinyl Chloride) Matrix Membrane Electrodes for the Selective Determination of Cocaine in Illicit Powders," Talanta, 1992, vol. 39, No. 10, pp. 1329-1335.

L. Campanella, C. Colapicchioni, M. Tamossetti, A. Bianco & S. Dezzi, "A new ISFET device for cocaine analysis," Sensors and Actuators, 1995, vol. 24-25, pp. 188-193.

Kiyoyuki Watanabe, Kunio Okada, Hideo Oda, Katsushi Furuno, Yutaka Gomita & Takashi Katsu, "New cocaine-selective membrane electrode," Anal. Chim. Acta, 1995, vol. 316, pp. 371-375.

Kiyoycki Watanabe, Kunio Okada & Takashi Katsu, "Development of an Amphetamine-Selective Electrode," Jpn. J. Toxicol. Environ. Health, 1996, vol. 42, p. 33.

Saad S. M. Hassan & Eman M. Elnemma, "Amphetamine Selective Electrodes Based on Dibenzo-18-crown-6 and Dibenzo-24-crown-8 Liquid Membranes," Anal. Chem., 1989, vol. 61, pp. 2189-2192.

Kiyoyuki Watanabe, Kunio Okada, Hideo Oda & Takashi Katsu, "Development of a Portable Cocaine-Selective Electrode," Jpn. J. Toxicol. Environ. Health, 1997, vol. 43, p. 17.

L. Campanella, L. Aiello, C. Colapicchioni & M. Tomassetti, "Lidocaine and benzalkonium analysis and titration in drugs using new ISFET devices," J. Pharm. Biomed. Anal., 1998, vol. 18, pp. 117-125.

L. Campanella, C. Colapicchioni, M. Tomassetti & S. Dezzi, "Comparison of three analytical methods for cocaine analysis of illicit powders," J. Pharm. Biomed. Anal., 1996, vol. 14, pp. 1047-1054.

Saad S. M. Hassan, Eman M. Elnemma & Eman H. El-Naby, "Solid-State Planar Microsensors for Selective Potentiometric Determination of Ethylmorphine," Anal. Let., 1999, vol. 32, pp. 271-285.

Eman M. Elnemma & M. A. Hamada, "Plastic Membrane Electrodes for the Potentiometric Determination of Codeine in Pharmaceutical Preparations," Mikrochim Acta, 1997, vol. 126, pp. 147-151.

Larry Cunningham & Henry Freiser, "Ion-Selective Electrodes for Basic Drugs," Anal. Chim. Acta., 1982, vol. 139, pp. 97-103.

Charles R. Martin & Henry Freiser, "Ion-Selective Electrode for the Determination of Phencyclidine," Anal. Chem., 1980, vol. 52, pp. 1772-1774.

Gary D. Carmack & Henry Freiser, "Assay of Phenobarbital with an Ion-Selective Electrode," Anal. Chem., 1977, vol. 49, No. 11, pp. 1577-1579.

Vasile V. Cosofret & Richard P. Buck, "Recent Advances in Pharmaceutical Analysis with Potentiometric Membrane Sensors," Critical Reviews in Analytical Chemistry, 1993, vol. 24, pp. 1-58.

Kiyoyuki Watanabe, Kunio Okada, Hideo Oda & Takashi Katsu, "Development of a portable cocaine-selective electrode," Bunseki Kagaku, 1997, vol. 46, No. 12, pp. 1019-1023.

Sebojka Komorsky-Lovric, Iva Galic & Rahela Penovski, "Voltammetric Determination of Cocaine Microparticles," Electroanalysis, 1999, vol. 11, No. 2, pp. 120-123.

T. C. W. Yeow, M. R. Haskard, D. E. Mulcahy, H. I. Seo & D. H. Kwon, "A very large integrated pH-ISFET sensor array chip compatible with standard CMOS processes," Sensors and Actuators, 1997, vol. 44, pp. 434-440.

Hyuk Jin Lee, Uk Sun Hong, Dong Kwon Lee, Jae Ho Shin, Hakhyun Nam & Geun Sig Cha, "Solvent-Processible Polymer Membrane-Based Liquid Junction-Free Reference Electrode," Anal. Chem., 1998, 70, 3377-3383.

* cited by examiner

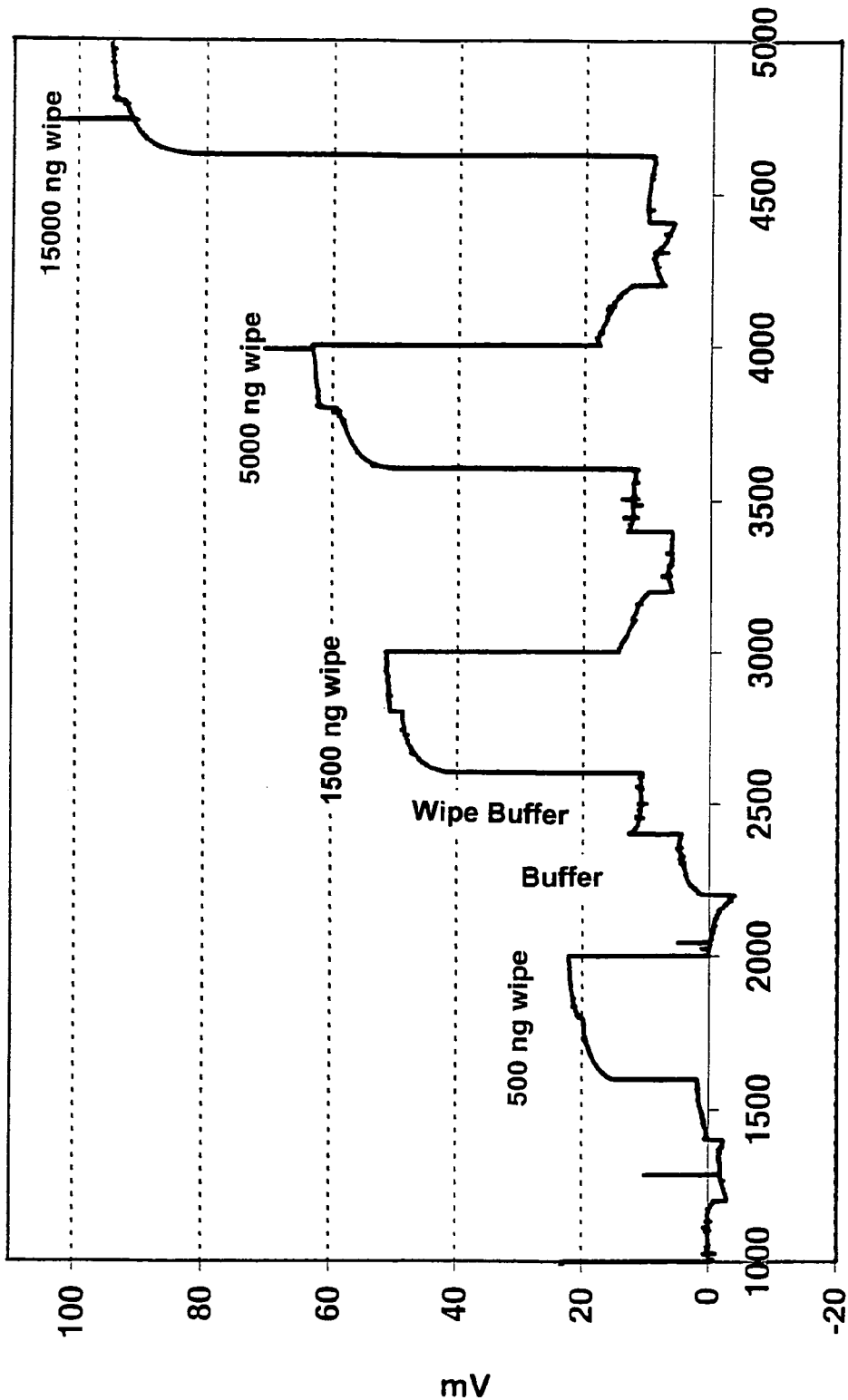

CAST MEMBRANE REFERENCE ELECTRODE AND METHOD OF MAKING

This is a continuation application of application Ser. No. 10/237,074, now U.S. Pat. No. 6,780,307 B2, filed on Sep. 9, 2002, the entire contents of which are incorporated herein by reference.

PRIORITY CLAIM

The present application claims priority from U.S. Provisional Application No. 60/328,423 filed Oct. 12, 2001, entitled "Ion selective electrodes for direct organic drug analysis in saliva, sweat, and surface wipes".

BACKGROUND

1. Field of the Invention

The present invention relates to ion selective electrodes and more specifically to ion selective electrodes for detecting organic drugs in saliva, sweat, and surface wipes.

2. Description of the Related Art

It is currently estimated that there are over three million hardcore cocaine users and one million hardcore heroin users in the United States. It is also estimated that there are over two million occasional cocaine users and half a million occasional heroin users. Together they consumed 269 metric tons of cocaine and 12.9 metric tons of heroin in 2000 spending $63 billion on illicit drugs. Rhodes, W., Layne, M., Johnston, P., Hozik, L., *What America's Users Spend on Illegal Drugs 1988-1998*, Office of National Drug Control Policy, December 2000. One adverse consequence of drug use that appears to be grossly under-publicized is driving under the influence of drugs. Although alcohol contributes to about 39% of the 40,000+ annual fatal traffic accidents and 1.4 million arrests per year, a substantial fraction of those under the influence of alcohol are also under the influence of drugs. Shults, R., Impaired Driving, Dec. 11, 1998, CDC, National Center for Injury Prevention & Control. In a recent study conducted in Nassau County, N.Y. and Houston, Tex., about 36% of 800 drivers arrested for driving while intoxicated also had drug metabolites in their urine. See Hersch, R. K., Crouch, D. J., and Cook, R. F., "*Field Test of On-Site Drug Detection Devices*," DOT HS 809-192, October 2000 and Brookoff, D., Cook, C. S., Williams, C., and Mann, C. S. "*Testing Reckless Drivers for Cocaine and Marijuana*", N Engl J Med, 331(8): 518-522 (1994) for similar results. Another study showed that 45% of federal prisoners have driven a car while under the influence of drugs (www.ojp.usdoj.gov/bjs). Thus, driving under the influence of drugs (DUID) is a critically important public safety issue.

Campaigns such as Mothers Against Drunk Driving have reduced alcohol-related automobile fatalities over 30% in the past decade. One of the factors that appears to dissuade public interest groups from starting similar campaigns against DUID is the lack of effective tools in the hands of law enforcement officers to rapidly and privately measure drug levels. Once those tools are made widely available, a serious and credible deterrent to occasional drug use would be present. The publicity would both reduce DUID and help make illicit drug use socially unacceptable in the public eye.

During routine traffic stops or DWI (driving while intoxicated) roadblocks, police officers have only a few moments to determine if a driver is under the influence. Besides the usual visual clues, the main tool in current use is the Officer's sense of smell, which works in a limited way only for alcohol and marijuana. Frequently, individuals who consume drugs also consume alcohol, which provides a synergistic effect. If the alcohol level is below the legal limit, the police officer must make a decision on an arrest. Other drugs of abuse do not provide overt signs of use unless an individual is substantially impaired. Thus, a rapid, fieldable instrument assisting in this decision process would help detect and deter DUID if widely employed.

Urine and blood can be tested to detect drug use. However, the non-private collection method and the long window of detection of drugs in urine (days to weeks) are considered by many to be an invasion of privacy and may not be reflective of the actual safety hazard posed by use of drugs while driving.

Other media, such as saliva and sweat, can also be tested to detect drug use. As shown in FIG. 1, after the first few minutes of use, levels of cocaine in saliva parallel levels in plasma, which are better associated with impairment. If a cocaine cut-off level were set at approximately 50 ng/mL, the window of detection for cocaine in saliva would only be four hours. Because cocaine can only be detected during this short timeframe following cocaine administration, it is easier to demonstrate some impairment in driving performance compared to the several days that urine would test positive. In some operational scenarios, saliva may be too intrusive. Instead, a skin swab may be employed. Although skin swabs measure both passive exposure and use, the absence of drug residues would rule out drug use, except under extraordinary circumstances.

Current technologies to detect drugs in saliva include ion mobility mass spectrometry and immunoassays. Ion mobility mass spectrometry, as exemplified by the Barringer Ion Scan and the Barringer Sabre 2000 (www.barringer.com) or the Ion Track Itemiser and the Ion Track VaporTracer-2 (www.iontrack.com), has the advantage of rapid (1 minute) detection of a wide variety of materials in a semi-quantitative manner. However, it has the disadvantages of high cost ($20K-$42K/unit), maintenance, and bulk (shoe-box to suitcase sized). Immunoassays, as exemplified by Securetec Drugwipes (www.securetec.net), have the advantage of simplicity of operation, portability, and low cost (<$10/each). U.S. Pat. No. 5,891,649, incorporated herein by reference, discloses the use of immunoassays for detection of drugs in sweat. However, immunoassays are selective for each drug or drug class, and therefore, a separate test must be performed for each substance suspected. Also, they are non-reusable so the reoccurring costs may be prohibitive in high volume applications. In addition, immunoassays only provide a presence or absence indication; quantitative analysis is difficult without instrumentation and then it is linear only over a limited range.

Another technology to detect drugs is ion selective electrodes, which measure ionic species. Ion selective electrodes are well known in the art to measure ionic species such as potassium, lithium, sodium, and calcium. However, developing ion selective electrodes to detect drugs has been limited to detecting drugs in pharmaceutical preparations or to detecting illicit drugs in urine or blood. Information relevant to using ion selective electrodes can be found in the following references: Elnemma, E. M., Hamada, M. A. and Hassan, S. S. M., "*Liquid and Poly (Vinyl Chloride) Matrix Membrane Electrodes for the Selective Determination of Cocaine in Illicit Powders*," Talanta, 39 1329-1335 (1992); Campanella, L., Colapicchioni, C., Tomassetti, M., Bianco, A. and Dezzi, S., "*A New ISFET Device for Cocaine Analysis*," Sensors and Actuators, 24-25 188-193 (1995); Watanabe, K., Okada, K., Oda, H., Furuno, K., Gomita, Y. and Katsu, T., "*New Cocaine-Selective Membrane Electrode*," Analytica Chimica Acta, 316 371-375 (1995); K. Watanabe, K. Okada, and T. Katsu, "*Development of an Amphetamine-Selective Electrode*," Jpn.

J. Toxicol. Environ. Health, 42, 33 (1996); S. S. M. Hassan and E. M. Elnemma, "*Amphetamine Selective Electrodes Based on dibenzo-18-crown-6 and dibenzo-24-crown-8 Liquid Membranes*," Anal. Chem., 61 2189-2192 (1989); K. Watanbe, K. Okada, H. Oda, and T. Katsu, "*Development of a portable cocaine-selective electrode*," Jpn. J. Toxicol. Environ. Health, 43, 17(1997); L. Campanella, L. Aiello, C. Colapicchioni, and M. Tomassetti, "*Lidocane and Benzalkonium Analysis and Titration in Drugs Using New ISFET Devices*," J. Pharm. Biomed. Anal., 18 117-125 (1998); L. Campanella, C. Colapicchioni, M. Tomassetti, and S. Dezzi, "*Comparison of Three Analytical Methods for Cocaine Analysis of Illicit Powders*," J. Pharm. Biomed. Anal., 14 1047-54 (1996); S. S. M. Hassan, E. M. Elnemma, and E. H. El-Naby, "*Solid State Planar Microsensors for Selective Potentiometric Determination of Ethylmorphine*," Anal. Let., 32 271-285 (1999); E. M. Elnemma and M. A. Hamada, "*Plastic Membrane Electrodes for the Potentiometric Determination of Codeine in Pharmaceutical Preparations*," Mikrochim Acta, 126 147-151 (1997); L. Cunningham and H. Freiser, "*Ion-Selective Electrodes for Basic Drugs*," Anal. Chim. Acta., 139 97-103 (1982); C. R. Martin and H. Freiser, "*Ion-Selective Electrodes for the Determination of Phencyclidine*," Anal. Chem., 52 1772-1774 (1980); G. D. Carmack and H. Freiser, "*Assay of Phenobarbital with an Ion-Selective Electrode*," Anal. Chem., 49 1577-1579 (1977); Cosofret, V. V. and Buck, R. P., "*Recent Advances in Pharmaceutical Analysis with Potentiometric Membrane Sensors*," Critical Reviews in Analytical Chemistry, 24, 1-58 (1993); K. Watanbe, K. Okada, H. Oda, and T. Katsu, "*Development of a Portable Cocaine-Selective Electrode*," Bunseki Kagaku, 46 1019-1023 (1997); S. Komorsky-Lovric, I. Galic, and R. Penovski, "*Voltammetric Determination of Cocaine Microparticles*," Electroanalysis, 11 120-123 (1999); T. Yeow, M. R. Haskard, D. E. Mulcahy, H. I. Seo, and D. H. Kwon, "*A Very Large Integrated pH-ISFET Sensor Array Chip Compatible with Standard CMOS Processes*," Sensors Actuators B 44 434-440 (1997); U.S. Pat. No. 5,522,978; U.S. Pat. No. 5,914,271; U.S. Pat. No. 5,180,481; U.S. Pat. No. 6,212,418; U.S. Pat. No. 6,087,182; U.S. Pat. No. 6,165,796; U.S. Pat. No. 6,033,914; U.S. Pat. No. 5,531,870; U.S. Pat. No. 5,554,339; U.S. Pat. No. 5,753,519; U.S. Pat. No. 4,713,165; U.S. Pat. No. 4,454,007; and U.S. Pat. No. 4,399,002, all of which are incorporated herein by reference.

SUMMARY

The aforementioned problems with the current technologies are overcome by the present invention wherein a handheld, fieldable drug monitoring system can detect and quantitate cocaine and other carbon-based drugs of abuse in saliva, sweat, and surface wipes by using an ion selective electrode. In a preferred embodiment, an array of ion selective electrodes is used to detect and quantitate a variety of drugs of abuse.

In a preferred embodiment, the ion selective electrode of the present invention has a cast membrane reference electrode and a sensing electrode with a semi-permeable ion selective membrane comprising a hydrophobic polymer, a plasticizer, and an ionophore selective for the organic drug to be tested. In another aspect of the invention a device to detect organic drugs includes at least one ion selective electrode connected to a converter that coverts a voltage reading from the ion selective electrode to a quantitative drug concentration level. Yet another aspect of the invention is a method for detecting organic drugs in saliva, sweat, and surface wipes including the steps of (a) placing the ion selective electrode in a person's mouth, taking saliva from a person's mouth and placing the saliva on the ion selective electrode, squeezing a damp surface swab onto the ion selective electrode after wiping a surface, or wiping a surface after wrapping a damp surface swab around the ion selective electrode; (b) ensuring that the ion selective electrode has electrical contact; and (c) converting a voltage reading from the ion selective electrode to a quantitative drug concentration by using a concentration curve. Another aspect of the invention is a method for testing electrical contact in an ion selective electrode including the steps of (a) injecting a voltage pulse into a reference electrode; and (b) determining if there is a corresponding voltage pulse in a sensing electrode. Still another aspect of the invention is a method of making a cast membrane reference electrode including the steps of (a) casting an ionophoric membrane over a hole; (b) filling the interior of the hole with a salt solution; (c) placing a wire into the solution; and (d) sealing the hole.

The present invention results in several advantages. Testing for drugs in saliva, sweat or surface wipes is not invasive to a person's privacy and does not have a long window of detection, which makes it easier to determine a person's impairment. Moreover, by using an array of ion selective electrodes to detect drugs, there is rapid detection of a wide variety of drugs in a quantitative manner with low cost, low maintenance, and small size.

Anticipated system applications include roadside sobriety checks by direct testing of saliva, testing for traces of drugs in sweat using a surface wipe or skin swab, and identifying cocaine-containing items using a surface wipe to test for trace drug residues. Another potential application is a reverse drug test. Sometimes, people can present a threat to the public if they don't take certain drugs, e.g., anti-psychotic and anti-TB drugs. One can envision a case worker visiting an individual under treatment on a random basis, obtaining a saliva sample or skin swab, and testing the specimen in the presence of the test individual. The presence of the proper drug or metabolite above a given level would indicate that the individual was complying with the treatment regime. The absence of the drug or metabolite would indicate that further monitoring or in-patient treatment of the individual would be necessary. The present invention provides a quick, easy, and non-invasive method for determining whether a person has taken necessary drugs.

BRIEF DESCRIPTION OF THE DRAWINGS

These and other objects, features and advantages of the invention, as well as the invention itself, will become better understood by reference to the following detailed description, appended claims, and accompanying drawings where:

FIG. 9 shows the results of the surface wipe analysis from Example 6.

DETAILED DESCRIPTION

Figure 1:
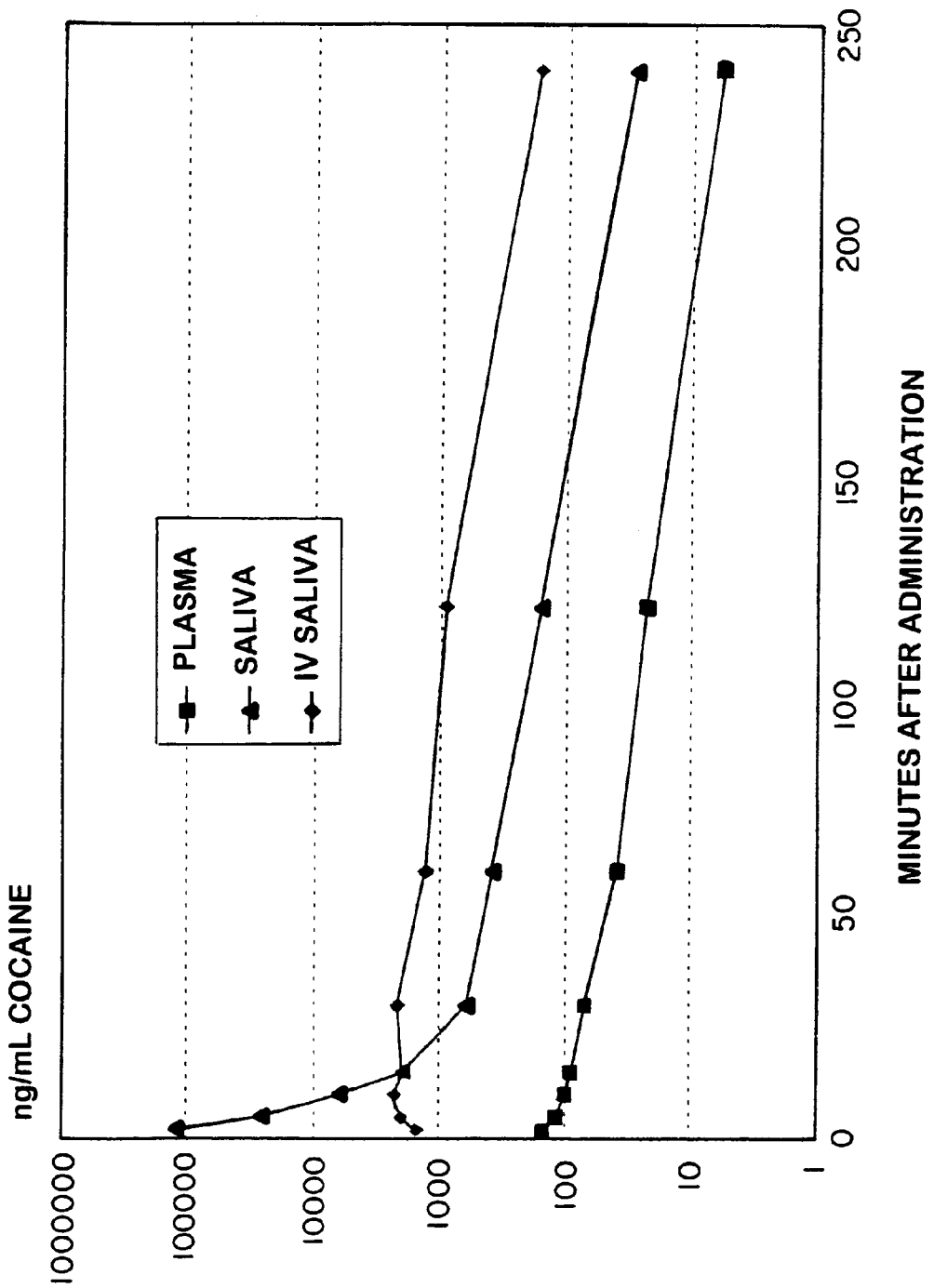
FIG. 1 compares levels of cocaine in saliva and plasma over time.

A hand-held, fieldable, drug monitoring system according to a preferred embodiment of the present invention uses at least one ion selective electrode to detect the presence of cocaine and other carbon-based drugs in saliva, sweat, and surface wipes and to quantitate the amount of drugs present. The system may consist of a single ion selective electrode to detect one drug or, preferably, an array of ion selective electrodes to detect multiple drugs. In addition to drugs, the monitoring system can also measure other parameters such as pH, potassium levels, sodium levels, or calcium levels, which can be useful for control and interference removing purposes. For example, for a response from an ion selective electrode, the analyte must be charged. The pKa of cocaine is about 8.6. Thus, at pH levels below 8.6, cocaine can be detected. At pH levels greater than 8.6, cocaine cannot be detected. By measuring pH and cocaine simultaneously, one can be assured of working at the proper pH range to detect cocaine. As another example, some ion selective membrane compositions show interference from potassium ions. This interference can be compensated if the potassium concentration is measured separately. (For the purposes of this application, concentration is equal to activity.)

The ion selective electrode or array of ion selective electrodes can obtain readings from saliva, sweat, or a surface wipe in several ways including: (1) placing the ion selective electrode or array in a person's mouth; (2) taking saliva from a person's mouth and placing the saliva on the ion selective electrode; (3) squeezing a damp surface swab onto the ion selective electrode or array after wiping a surface; and (4) wrapping a damp surface swab around the ion selective electrode or array and then wiping a surface. The array of ion selective electrodes is connected to a programmable digital microconverter, which can have amplification and noise reduction. The system may be powered by an internal battery or a Pocket PC computer, and the data may be relayed via wire connections, infrared telemetry, or other wireless links.

Ion selective electrodes can contain different types of sensors. In the present invention, the term ion selective electrode is considered to include liquid membrane types of ion selective electrodes, polymer membrane types of ion selective electrodes, solid-state ion-selective electrodes, and ion-selective, field effect transistors.

An ion selective electrode, which is equivalent to a battery, contains two poles where electrons originate and conclude to complete an electrical circuit: a sensing electrode and a reference electrode. For membrane-type electrodes, such as liquid filled or wire coated electrodes, a semi-permeable membrane separates the two poles. Ions are carried across the semi-permeable membrane with a selective transporter molecule—the driving force being a concentration gradient on either side of the membrane. Because the transport molecule carries only one part of the ion pair (e.g. the cation for cocaine), a charge build-up occurs inside the ion selective electrode solution. This charge build-up generates a voltage that can be measured and resists further diffusion of analyte cations. With higher concentrations of analyte, the voltage will be higher.

Figure 2:
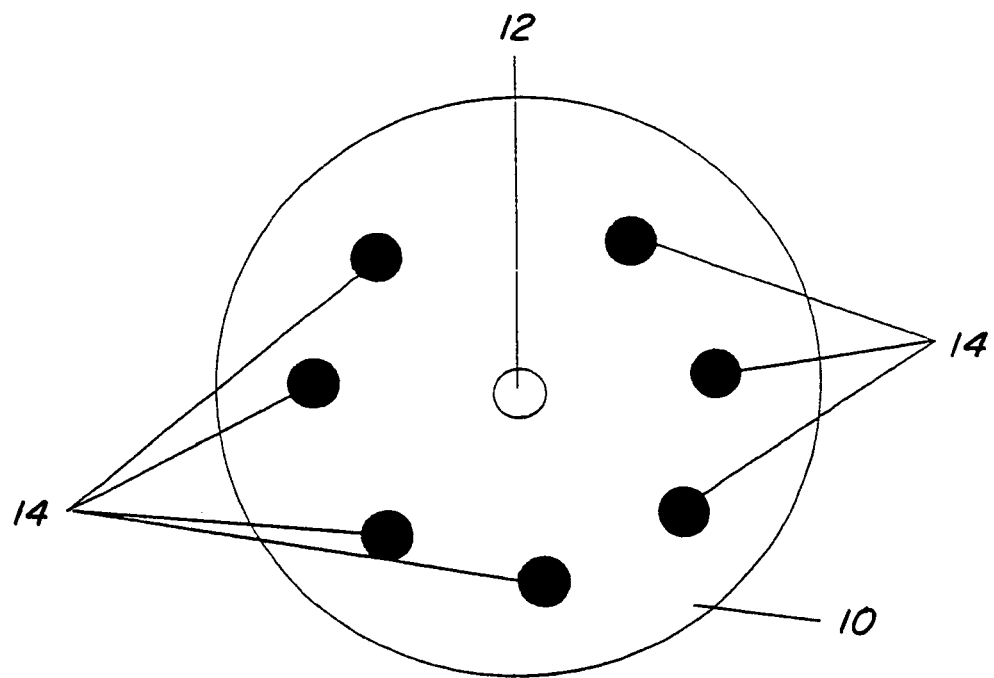
FIG. 2 is a top view of an ion selective electrode.

A drug monitoring system in accordance with a preferred embodiment of the present invention generally includes a reference electrode, at least one but preferably an array of sensing electrodes each with a semi-permeable ion selective membrane, and a converter to convert a voltage reading from the ion selective electrode to a quantitative drug concentration level. As shown in FIG. 2, the reference electrode and sensing electrodes are typically housed in a plastic rod 10, preferably a PVC rod. Other materials, such as Tygon® tubing, can be used for the electrode body. Holes can be drilled into the rod 10 for the electrodes. A hole is drilled in the center of the rod 10 for the reference electrode 12, and at least one but preferably 6-7 holes are drilled in a circular format around the perimeter of the rod for the sensing electrodes 14. Alternatively, the holes for the reference electrode 12 and sensing electrodes 14 can be drilled anywhere in the rod 10, and any number of holes can be drilled for the sensing electrodes 14 depending on how many sensing electrodes are desired. The rod 10 used to house the electrodes can be any size, and it can be planar.

Reference Electrode

To allow accurate readings in a widely varying media, most reference electrodes use a concentrated salt solution as an inner filling solution and a porous plug to make electrical contact with the test solution. The porous plug acts as a small leak for the inner salt solution. Typical porous materials are porous glass frits, cracked glass, fiber, gels (which tend to dry out and thereby fail), or a small hole (which requires frequent refilling of the reference electrode). Using these types of porous materials makes manufacturing the ion selective electrode difficult because of the manual placement of the plug or the reproducible preparation of the hole. Furthermore, porous plugs can plug-up causing the ion selective electrode to fail. To avoid these problems and ease manufacturing, the present invention uses a porous membrane that can be cast into place, thereby allowing easy assembly. Additionally, the membrane performance does not degrade when allowed to "dry" out. After being left unprotected at room temperature, the ion selective electrode provides a stable signal within a few minutes of rehydration.

Using a castable reference electrode allows water-soluble (hydrophilic) polymers to form immiscible solutions in host (hydrophobic) polymers, such as polyvinyl chloride (PVC). The hydrophobic polymers form the membrane and provide support. The hydrophilic polymers may either be leached from the hydrophobic polymer forming pores through which ions may flow or remain in the hydrophobic polymer and act as ion carriers. Examples of hydrophilic polymers include polyethylene glycol and polypropylene glycol in a wide variety of molecular weights, but those with lower molecular weights work better (see Table 1).

Figure 3:
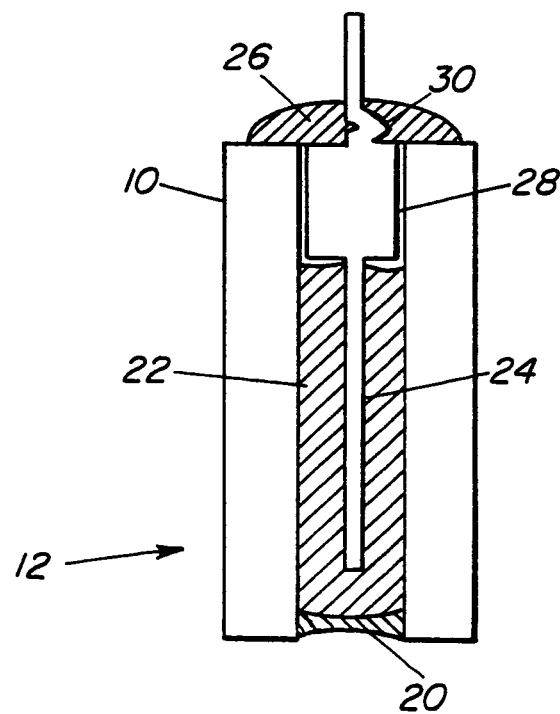
FIG. 3 is a sectional view of a reference electrode.

As shown in FIG. 3, to form the reference electrode 12, a membrane solution is used that consists of a hydrophobic polymer, preferably PVC, and a hydrophilic polymer, preferably polyethylene glycol with molecular weight 1450, in varying ratios, preferably 1:2 parts by weight of PVC to polyethylene glycol in a compatible solvent, preferably tetrahydrofuran. Approximately 5 µl of the membrane solution at room temperature is placed at the bottom end of the center hole drilled in the PVC rod 10, and surface tension keeps the liquid completely across the hole. The rod 10 is held vertically for a few minutes until the solution sets and is then allowed to completely dry to form a semi-permeable membrane 20. Preferably the solution is allowed to dry overnight at room temperature, or alternatively it can dry for approximately 30 minutes at room temperature and then 30 minutes at 60° C. The membrane 20 should be translucent and should completely cover the hole. The closer the membrane 20 is to the end of the rod 10, the better the electrode performance. Membranes that are recessed slightly can have pockets where mixing with the bulk solution is slow and thereby result in poorer electrode performance.

The electrode is filled from the top end of the drill hole with a salt solution 22, such as $NaNO_3$, KCl, $Na_2SO_4$, NaF, or LiF but preferably NaCl, by using a gel filling pipette tip placed inside the chamber and slowly withdrawing the tip as liquid is dispensed. Air bubbles should be avoided. A wire 24, preferably a silver wire coated with AgCl, is placed in the top at least halfway down in the filling solution and sealed, preferably with epoxy 26. The wire 24 can have a very short piece of heat-shrunk tubing 28 that acts as a sleeve. This tubing 28 both reduces the sealing distance required of the epoxy 26 and helps center the silver wire 24 in the reference body. The silver wire may be bent into a sharp S shape 30 at the top of the electrode to help allow the epoxy 26 hold the wire 24 in place. The AgCl coated silver wire is either made by oxidizing silver electrically in a KCl solution or more preferably by using a $FeCl_3$ solution used to etch printed circuit boards as sold by GC Thorsen, Inc., Rockford, Ill.

Sensing Electrode

The sensing electrode is prepared in a similar way as the reference electrode. The membrane solution for the sensing electrode consists of a hydrophobic polymer such as PVC, a plasticizer, and at least one ionophore that is selective for the drug to be tested. A membrane solution is preferably prepared by mixing varying proportions of premixed stocks of the following components in a tetrahydrofuran (THF) solvent:

(1) 100 mg/mL PVC high molecular weight;

(2) 100 mg/mL plasticizer selected from the following list: bis(2-ethylhexyl) sebacate, octyl [2-(trifluoromethyl) phenyl]ether, chloroparaffin, Santovac 5, bis (2-ethylhexyl) malenate, tris(2-ethylhexyl)trimellitate, 2-nitrophenyl octyl ether, bis(2-ethylhexyl)hydrogen phosphate, dioctyl phthalate, and mixtures of these materials;

(3) 10 mg/mL of ionophore cocaine cobalt isothiocyanate or cocaine chromium isothiocyanate, preferably cocaine cobalt isothiocyanate (cocaine tetraphenyl borate, cocaine dinonylnaphthalene disulfonic acid, and cocaine dinonylnaphthalene sulfonic acid can also be used to test for cocaine. To test for organic drugs other than cocaine, different ionophores can be used in the membrane solution); and (4) optionally 10 mg/mL ionophore selected from the following list: tetrakis(4-chlorophenyl)borate, trioctyl phosphine oxide, tetrakis [3,5-bis(1,1,1,3,3,3-hexafluoro-2-methoxy-2-propyl)phenyl]borate, tetrakis [3,5-bis-(trifluoromethyl) phenyl]borate, tetraphenyl borate, tetrakis [3.5-bis(trifluoromethyl)phenyl]borate, other borate sales, and mixtures of these substances with various counter-ions.

Typical sebacate mixtures consist of 1:1, 1:1.5 and 1:2 PVC to plasticizer ratios each containing 1% by weight cocaine ionophores. Typical Santovac 5 mixtures contain 1:1.8 and 1:3.5 PVC to plasticizer ratios with approximately 0.6% cocaine ionophores. Optionally, membranes may be made with about 0.1% to 5% of an additional ionophore.

In addition, a buffering agent and anions can be used in the membrane filling solution. Buffers generally consist of 0.05 M sodium or magnesium acetate, pH 4.5. Solutions buffered with citrate, tartrate, phosphate, formate, proprionate and trifluoroacetate of similar molarities and varying pH can also be used. Large hydrophobic anions can be added to the membrane solution. The following 90 mM anions can be used: potassium chloride, magnesium chloride, potassium bromide, and potassium iodide. There appears to be no significant effect when varying either the buffer or anion.

Cocaine cobalt isothiocyanate can be prepared by mixing cocaine hydrochloride in water with equal molar amounts of sodium cobalt isothiocyanate and filtering the blue precipitate, washing with water, and air drying. Cocaine chromium isothiocyanate can be prepared similarly.

To form the cast membrane for a liquid filled electrode, pipette 5 µL of membrane solution into the drilled hole of the plastic rod. Allow the membrane to dry overnight. Fill the electrode from the top end of the drill hole with a salt solution, such as KCl, $NaNO_3$, NaF, LiCl, or LiF but preferably NaCl. Place a wire, preferably a silver wire coated with AgCl at least halfway down in the filling solution and seal the top, preferably with epoxy. The AgCl coated silver wire can be made either by oxidizing silver electrically in a KCl solution or more preferably by using $FeCl_3$ solution used to etch printed circuit boards as sold by GC Thorsen, Inc., Rockford, Ill.

To form a single wire-coated sensing electrode, take an insulated wire such as an 18-gauge insulated wire, polish the end of the wire, dip the polished end in the membrane solution, and dry overnight. Arrays of wire-coated electrodes can be made by drilling several holes in a plastic rod, preferably a ½" PVC rod, inserting 18-gauge bare wires (either copper or silver with no effect on the results), gluing in place, polishing at one end, and then covering the bare wire with 5-10 µL of various membrane solutions and allowing to air dry. PVC rod is preferred for good adhesion of the PVC membrane.

For an array of ion selective electrodes, prepare a membrane solution for each sensing electrode. The ionophore will vary because the ionophore is selective for the drug to be tested. Each sensing electrode can be prepared as explained above.

Indication of Electrical Contact

Ion selective electrodes may have either a positive potential or negative potential in reference to the reference electrode. This requires bipolar circuitry on all the analogue components. Although readily achievable by using two batteries, a DC-DC converter, or a voltage divider, the added complexity and cost is unnecessary. An alternative design is to use a voltage divider to bias the reference part of the ion selective electrode (for example the MAX406, MAX407, MAX409, and MAX417-MAX419 operational amplifiers by MAXIM (www.maxim-ic.com)). Alternatively, a variable offset voltage (generated using a digital to analog converter) can bias the ion selective electrode in a variable manner to accommodate different ion selective electrodes. This also allows a microprocessor to determine if the ion selective electrode is in contact with a solution.

An ion selective electrode may produce unstable and variable readings when not in contact with a test solution. Most ion selective electrodes do not have a means of determining if the ion selective electrode is in solution and properly working. Because the present invention may be used to test saliva inside a person's mouth, if the person does not produce sufficient saliva to make electrical contact between the reference and sensing electrodes, the voltage reading will be in error.

With an open circuit (e.g. no saliva), the voltage reading could be anything depending on the voltage leakage on the printed circuit board and the humidity in the air. A person observing the signal from the ion selective electrode could observe considerable noise and scatter in the signal levels until electrical contact was complete. This variation in signal level would lessen the confidence of the user that the instrument was performing properly.

A variable offset voltage allows the microprocessor to step the voltage in a controlled manner and observe the output of the ion selective electrode. A complete circuit occurs only if the output follows the offset voltage. For example, to test for a complete circuit, inject a voltage pulse (for example, 100 mV) into the reference electrode. Then monitor to detect that voltage pulse on the sensing electrode. If the voltage pulse (that is, the increase in voltage over the normal output of the ion selective electrode) is present in the appropriate intensity (here 100 mV), there is electrical continuity between those two points. If the voltage pulse is not present in the appropriate intensity, a warning message can be sent to the operator.

Response Data and Calibration Curve Methodology

Figure 4:
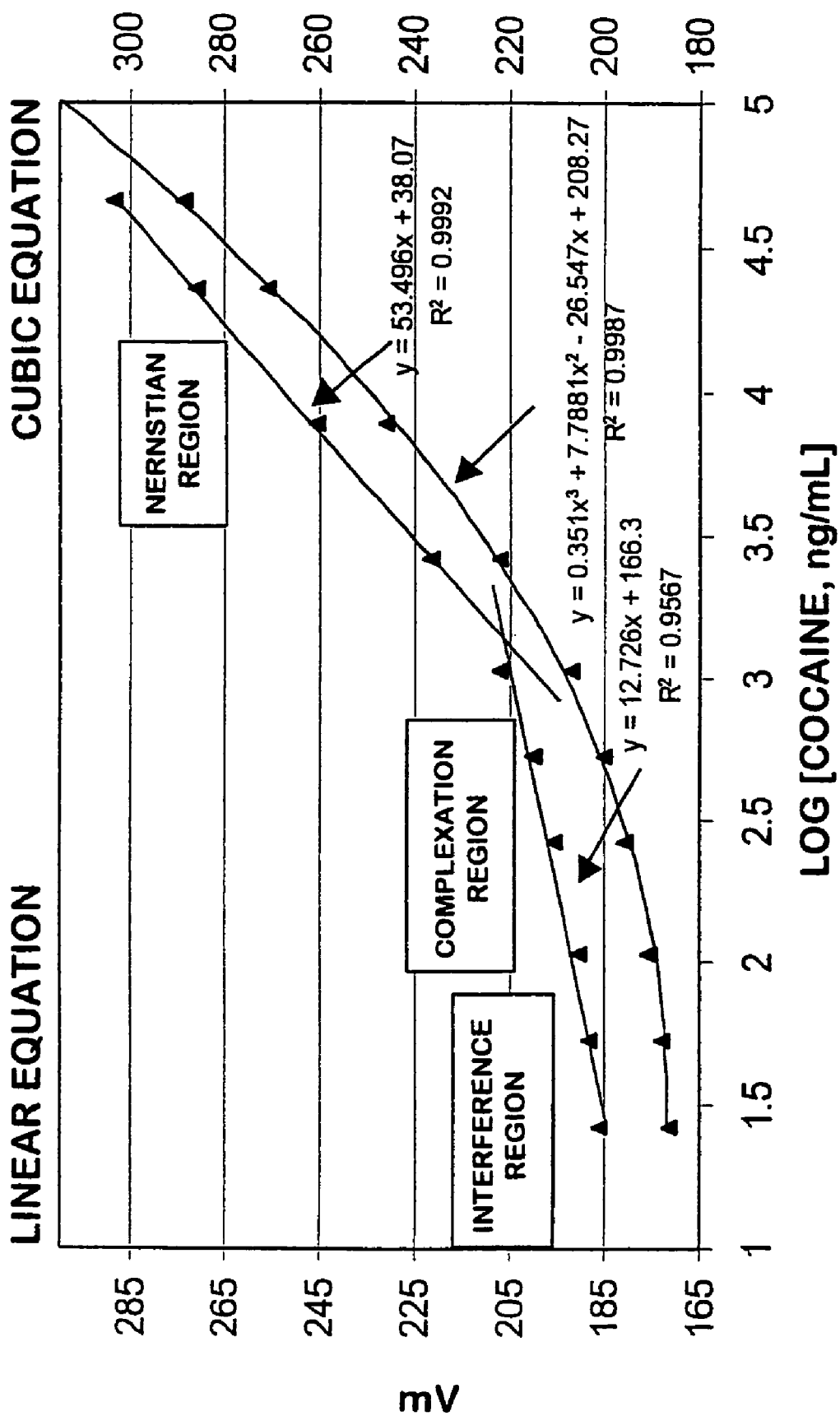
FIG. 4 shows the response of a cocaine sensor using both a linear and a polynomial fitting technique for the same data set with one technique using a second right-hand axis to offset the data set to better distinguish the fitting techniques.

FIG. 4 shows a representative response of one cocaine sensor over several decades of cocaine concentration. There are three major regions in this graph. The region of steeper slope is referred to as the Nernstian region. In this region, an equilibrium voltage is rapidly established as charged cocaine molecules diffuse across the membrane. The inside positive voltage resists further diffusion of cocaine. The linear region of lower slope may be attributed to the complexation constant for the carrier molecule. When the concentration of cocaine in the test solution becomes lower than the value of the complexation constant, the number of molecules traversing the membrane will be reduced to a level below that required to bias the gain stage of the detection circuit. Because of the electrical requirements of the measuring circuit, the electrode is essentially shorted and the voltage drops. The last region, which is at very low cocaine concentrations, is dominated by interfering positively charged ions and has a slope of zero. The region can be extended to lower values of cocaine by choice of the buffer and membrane plasticizing agent.

There are three methods for establishing the limit of detection (LOD) of an electrode. First, there is the IUPAC definition, which says the LOD is that concentration where a difference of 18 mV or more exists between the measured potential and that predicted by the regression of the Nerstian line. Second, there is a more practical definition often used where the LOD is taken as the intersection point of the Nernstian line with the horizontal line determined from the limiting potential or the region where reducing concentrations no longer affect the measured potential. Third, one can take the lowest possible detectable value as the point above which the voltage just becomes greater than the baseline plus three times the absolute value of the standard deviation of the signal/noise (S/N). The latter two methods are preferred for the present invention.

To generate concentration data from the voltage readings of the sensor, calibration curves can be used. There are various approaches for establishing calibration curves. One thing to consider is whether to use a linear or a non-linear function. As shown in FIG. 4, both linear and non-linear functions can be used successfully to fit the same data set. A calibration curve can be generated using two linear portions; the intersection of the two calibration lines determines what linear line should be used for quantitation. Alternatively, a higher order polynomial may be used to fit the collective set. The advantage of the linear approach is that a single point calibration may be used to determine concentrations in an analysis sample. Additionally, the linear approach is preferred for ease of calculation when most samples fall in the lower linear concentration on the graph and exact quantitations are not necessary. However, for the linear approach one must know a priori an anticipated range in which the sample is likely to fall. The advantages of a higher order fit are that a single equation may be used to translate system voltages to concentrations and greater accuracy, by nature of the smoothness of the function, is likely around the region where a shift in the governing transport mechanism occurs. However, for a polynomial of degree n, one must have n+1 data points for calibration, and these data points should span regions over which the different governing transport mechanisms occur.

Another thing to consider is whether to adjust for drift. With time, almost all ion selective electrodes change their voltage readings for a given solution concentration. This is called drift, and there are various ways to compensate for drift. First, one can run a calibration curve before analyzing a sample. This is a reliable technique, but it can be time consuming because high accuracy requires several points to make up a curve. A compromise is to make a two-point calibration. Second, one can take the average parameters from linear or non-linear fits of calibration curves taken repeatedly over a period in which drift is present. Once done, compensation can be made by normalizing values to an average baseline or, as in the case of a one-point calibration, the average value at some particular concentration.

Example 1

Testing of Various Reference Membrane Compositions

Figure 5:
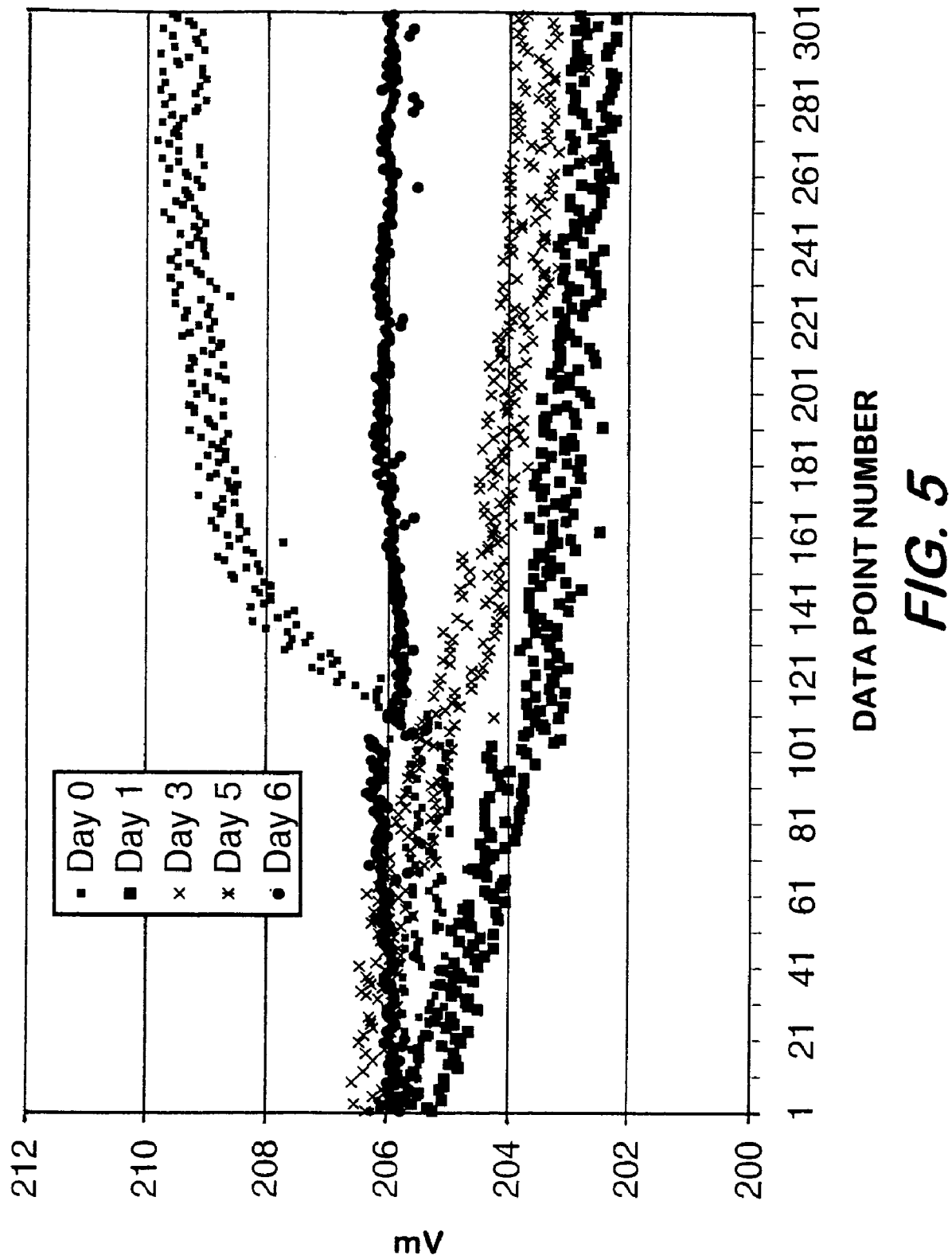
FIG. 5 shows the stability of a reference electrode from Example 1.

Table 1 shows various membrane solutions for castable reference electrodes. FIG. 5 shows the stability of a reference electrode made with Membrane D from Table 1. At approximately data point 100, the buffer solution was made up to 50 mM KCl for each curve. The reference electrode was artificially aged by storage at 37° C. without a covering. Data points were taken approximately once per second.

TABLE 1

Membrane solutions for castable reference electrodes

| Membrane Name | Solution mixture Parts by weight PVC:PEG MW 1450 | Comments |
|---|---|---|
| Membrane A | 500:100 | No response |
| Membrane B | 500:250 | No response |
| Membrane C | 500:500 | Some response |
| Membrane D | 500:750 | Good response, stable |
| Membrane F | 500:1000 | Stable reference for long periods, membrane has mechanical stability |

Various reference membranes using polyethylene glycol (PEG) and polypropylene glycol (PPG) were analyzed. The ratio of PEG or PPG to PVC was 2:1 by weight. For PEG, the molecular weights tested were 600, 1460, and 8000. For PPG, the molecular weights tested were 1000 and 2000. These membrane compositions were cast as an array of electrodes. The reference electrode was a saturated calomel electrode. The membrane compositions were monitored in 10 mL of $Mg(OAc)_2$ buffer. NaCl or $MgCl_2$ was added to test the change in ion activity and chloride concentration; little effect was observed. PEG is superior to PPG and lower molecular weights work better than higher molecular weights. PEG 1460 is preferred because of its structural integrity.

Example 2

Effect of Membrane Composition for Sensing Electrode

Table 2 shows the response and limit of detection for various membrane compositions. Table 3 shows average mV responses at 500 ng/mL ($1.65 \times 10^{-6}$ M free base) cocaine for a series of liquid filled electrodes having varying membrane compositions. Though the number of replicate sensors in this study is small and relative standard deviations are usually large, some general trends are apparent. First, with the cocaine cobalt isothiocyanate, larger amounts of plasticizer, up to a 1:2 PVC:sebacate ratio and a 1:3.5 PVC:Santovac 5/sebacate mix ratio result in electrodes with approximately double the response voltage from those for the 1:1 PVC:sebacate ratio. The opposite trend is shown for the cocaine chromium isothiocyanate with the lower 1:1 PVC:sebacate mix showing double the response of the 1:2 electrode. The 1:3.5 PVC:Santovac 5/sebacate mix ratio with the cocaine chromium isothiocyanate ionophore, given the % relative standard deviation (RSD) does not allow any certain conclusion about which is better than the other. However, electrodes were produced from both types with responses superior by 50-100% to the 1:1 PVC:sebacate mix.

TABLE 2

Response and Limit of Detection for various membrane compositions.

| Membrane Composition | Response and Limit of Detection |
|---|---|
| Cocaine chromium isothiocyanate, 2-Nitrophenyl octyl ether, Poly(vinyl chloride) (low molecular weight), Potassium tetrakis (4-chlorophenyl) borate, 1M sodium chloride reference | Response to 185 mV-LOD of 100 ng |
| Cocaine chromium isothiocyanate, 2-Nitrophenyl octyl ether, Poly(vinylidene chloride-co-acrylonitrile), Potassium tetrakis (4-chlorophenyl) borate, 1M sodium chloride reference | Response to 180 mV-LOD of 100 ng |
| Cocaine chromium isothiocyanate, 2-Nitrophenyl octyl ether, Poly(vinyl chloride), carboxylated, Potassium tetrakis (4-chlorophenyl) borate, 1M sodium chloride reference | Response to 170 mV-LOD of 3000 ng |
| Cocaine cobalt isothiocyanate, 2-Nitrophenyl octyl ether Poly (vinyl chloride)(low molecular weight), Potassium tetrakis (4-chlorophenyl) borate, 1M Sodium Chloride reference | Responds well - 215 mV-LOD of 1000 ng |
| Cocaine cobalt isothiocyanate, 2-Nitrophenyl octyl ether, Poly(vinylidene chloride-co-acrylonitrile), Potassium tetrakis (4-chlorophenyl) borate, 1M sodium chloride reference | Response to 175 mV-LOD of 100 ng |
| Cocaine cobalt isothiocyanate, 2-Nitrophenyl octyl ether, Poly (vinyl chloride), carboxylated, Potassium tetrakis (4-chlorophenyl) borate, 1M sodium chloride reference | Response to 180 mV-LOD of 100 ng |
| Cocaine chromium isothiocyanate, Bis(2-ethylhexyl) maleate, Poly(vinyl chloride) (low molecular weight), 1M potassium chloride reference | Response to 115 mV-LOD of 3000 ng |
| Cocaine chromium isothiocyanate, 2-Nitrophenyl octyl ether, Poly(vinyl chloride) (high molecular weight) 1M potassium chloride reference | Response to 130 mV-LOD of 1000 ng |
| Cocaine chromium isothiocyanate, 2-Nitrophenyl octyl ether, Poly(vinyl chloride) (low molecular weight), 1M potassium chloride reference | Response to 137 mV-LOD of 300 ng |
| Cocaine chromium isothiocyanate, 2-Nitrophenyl octyl ether, Poly(vinylidene chloride-co-acrylonitrile), 1M potassium chloride reference | Response to 140 mV-LOD of 300 ng |
| Cocaine chromium isothiocyanate, 2-Nitrophenyl octyl ether, Poly(vinyl chloride), carboxylated, 1M potassium chloride reference | Response to 115 mV-LOD of 1000 ng |
| Cocaine chromium isothiocyanate, 2-Nitrophenyl octyl ether, Poly(vinylidene fluoride) 1M potassium chloride reference | Response to 140 mV-LOD of 1000 ng |
| Cocaine chromium isothiocyanate, Bis (2-ethylhexyl) sebacate, | Response to 145 mV-LOD of 1000 ng |

TABLE 2-continued

Response and Limit of Detection for various membrane compositions.

| Membrane Composition | Response and Limit of Detection |
|---|---|
| Poly(vinylidene fluoride), 1M potassium chloride reference | |
| Cocaine chromium isothiocyanate, 2-Nitrophenyl octyl ether, Poly(vinylidene chloride-co-acrylonitrile), Potassium tetrakis (4-chlorophenyl) borate, 1M potassium chloride reference | Responds to 165 mV-LOD of 100 ng |
| Cocaine chromium isothiocyanate, 2-Nitrophenyl octyl ether, Poly(vinylidene chloride-co-acrylonitrile), Trioctylphosphine oxide, 1M potassium chloride reference | Responds to 185 mV-LOD of 100 ng |
| Cocaine chromium isothiocyanate, 2-Nitrophenyl octyl ether, Poly(vinylidene chloride-co-acrylonitrile), Potassium tetrakis [3,5-bis-(trifluoro methyl)phenyl]borate, 1M potassium chloride reference | Responds to 190 mV-LOD of 30 ng |
| Cocaine cobalt isothiocyanate, Bis (2-ethylhexyl) maleate, Poly(vinyl chloride) (high molecular weight), 1M potassium chloride reference | Response to 52 mV-LOD of 1000 ng Poor response |
| Cocaine cobalt isothiocyanate, Bis (2-ethylhexyl) maleate, Poly(vinylidene chloride-co-acrylonitrile), 1M potassium chloride reference | Response to 115 mV-LOD of 1000 ng |
| Cocaine cobalt isothiocyanate, 2-Nitrophenyl octyl ether, Poly(vinyl chloride) (high molecular weight), 1M potassium chloride reference | Response to 130 mV-LOD of 300 ng |
| Cocaine cobalt isothiocyanate, 2-Nitrophenyl octyl ether, Poly(vinyl chloride) (low molecular weight), 1M potassium chloride reference | Response to 130 mV-LOD of 1000 ng |
| Cocaine cobalt isothiocyanate, 2-Nitrophenyl octyl ether, Poly(vinylidene chloride-co-acrylonitrile), 1M potassium chloride reference | Response to 160 mV-LOD of 100 ng |
| Cocaine cobalt isothiocyanate, 2-Nitrophenyl octyl ether, Poly(vinyl chloride), carboxylated, 1M potassium chloride reference | Response to 115 mV-LOD of 1000 ng |
| Cocaine cobalt isothiocyanate, 2-Nitrophenyl octyl ether, Poly(vinylidene fluoride), 1M potassium chloride reference | Response to 80 mV-LOD of 3000 ng |
| Cocaine cobalt isothiocyanate, 2-Nitrophenyl octyl ether, Poly (vinyl chloride)(high molecular weight), Potassium tetrakis (4-chlorophenyl) borate, 1M potassium chloride reference | Responds well - 160 mV-LOD of 300 ng |
| Cocaine cobalt isothiocyanate, 2-Nitrophenyl octyl ether, Poly(vinyl chloride) (low molecular weight), Potassium tetrakis (4-chlorophenyl) borate, 1M potassium chloride reference | Response to 150 mV-LOD of 100 ng |
| Cocaine cobalt isothiocyanate, 2-Nitrophenyl octyl ether, Poly(vinylidene chloride-co-acrylonitrile), Potassium tetrakis (4-chlorophenyl) borate, 1M potassium chloride reference | Response to 170 mV-LOD of 100 ng |
| Cocaine cobalt isothiocyanate, 2-Nitrophenyl octyl ether, Poly(vinyl chloride), carboxylated, Potassium tetrakis (4-chlorophenyl) borate, 1M potassium chloride reference | Response to 160 mV-LOD of 100 ng |
| Cocaine cobalt isothiocyanate, 2-Nitrophenyl octyl ether, Poly(vinylidene fluoride), Potassium tetrakis (4-chlorophenyl) borate, 1M potassium chloride reference | Response to 110 mV-LOD of 1000 ng |
| Cocaine cobalt isothiocyanate, 2-Nitrophenyl octyl ether, Poly(vinylidene chloride-co-acrylonitrile), Trioctylphosphine oxide, 1M potassium chloride reference | Response to 200 mV-LOD of 30 ng |

TABLE 2-continued

Response and Limit of Detection for various membrane compositions.

| Membrane Composition | Response and Limit of Detection |
|---|---|
| Cocaine cobalt isothiocyanate, 2-Nitrophenyl octyl ether, Poly(vinylidene chloride-co-acrylonitrile), Tetrakis[3,5-bis(trifluoromethyl)phenyl]borate, 1M potassium chloride reference | Response to 200 mV-LOD of 100 ng |
| Cocaine cobalt isothiocyanate, 2-Nitrophenyl octyl ether, Poly(vinylidene chloride-co-acrylonitrile), Tetrakis[3,5-bis(1,1,1,3,3,3-hexafluoro-2-methoxy-2 propyl)phenyl]borate, 1M potassium chloride reference | Response to 210 mV-LOD of 30 ng |
| Cocaine tetraphenyl borate, 2-Nitrophenyl octyl ether, Poly(vinylidene chloride-co-acrylonitrile), 1M potassium chloride reference | Responds well - 180 mV-LOD of 100 ng |
| Cocaine Tetraphenyl borate, 2-Nitrophenyl octyl ether, Poly(vinyl chloride) (high molecular weight), Potassium tetrakis (4-chlorophenyl) borate. 1M potassium chloride reference | Response to 190 mV-LOD of 100 ng |
| Cocaine Tetraphenyl borate, 2-Nitrophenyl octyl ether, Poly(vinyl chloride) (low molecular weight), Potassium tetrakis (4-chlorophenyl) borate. 1M potassium chloride reference | Response to 170 mV-LOD of 100 ng |
| Cocaine tetraphenyl borate, 2-Nitrophenyl octyl ether, Poly(vinylidene chloride-co-acrylonitrile), Potassium tetrakis (4-chlorophenyl) borate, 1M potassium chloride reference | Responds well - 170 mV-LOD of 100 ng |
| Cocaine tetraphenyl borate, 2-Nitrophenyl octyl ether, Poly(vinylidene chloride-co-acrylonitrile), Trioctylphosphine oxide, 1M potassium chloride reference | Responds well - 205 mV-LOD of 100 ng |
| Cocaine tetraphenyl borate, 2-Nitrophenyl octyl ether, Poly(vinylidene chloride-co-acrylonitrile), Potassium tetrakis [3,5-(trifluoromethyl)phenyl]borate, 1M potassium chloride reference | Response to 195 mV-LOD of 3000 ng |
| Cocaine tetraphenyl borate, 2-Nitrophenyl octyl ether, Poly (vinylidene chloride-co-acrylonitrile), Tetrakis [3,5-bis(1,1,1,3,3,3-hexafluoro-2-methoxy-2-propyl)phenyl]borate, 1M potassium chloride reference | Responds well - 250 mV-LOD of 3000 ng Not as linear of a response. |
| Cocaine Tetraphenyl borate, 2-Nitrophenyl octyl ether, Poly(vinyl chloride), carboxylated, Potassium tetrakis (4-chlorophenyl) borate. 1M potassium chloride reference | Response to 140 mV-LOD of 300 ng |

TABLE 3

Comparison of electrode responses for varying membrane compositions. Average mV responses at 500 ng/mL ($1.65 \times 10^{-6}$ M free base) cocaine. Membranes compared in 50 mM sodium acetate buffer.

| Ionophore [%] | Plasticizer | PVC:Plasticizer | Number of Replicates | Average [mV × 3] | RSD |
|---|---|---|---|---|---|
| Cocaine cobalt isothiocyanate [1%] | Sebacate | 1:1 | 3 | 35.1 | 9.50% |
| | | 1:1.5 | 5 | 51.6 | 19.9% |
| | | 1:2 | 5 | 70.5 | 32.9% |
| Cocaine cobalt isothiocyanate [0.7%] | 1:1.4 Santovac 5: Sebacate | 1:1.8 | 4 | 49.8 | 27.0% |
| | | 1:3.5 | 5 | 70.4 | 18.9% |
| Cocaine chromium isothiocyanate [1%] | Sebacate | 1:1 | 3 | 66.3 | 11.0% |
| | | 1:1.5 | 3 | 13.8 | 0.83% |
| | | 1:2 | 3 | 28.9 | 8.44% |

TABLE 3-continued

Comparison of electrode responses for varying membrane compositions. Average mV responses at 500 ng/mL ($1.65 \times 10^{-6}$ M free base) cocaine. Membranes compared in 50 mM sodium acetate buffer.

| Ionophore [%] | Plasticizer | PVC:Plasticizer | Number of Replicates | Average [mV × 3] | RSD |
|---|---|---|---|---|---|
| Cocaine chromium isothiocyanate [0.66%] | 1:1.4 Santovac 5: Sebacate | 1:1.8 1:3.5 | 3 2 | 34.8 46.3 | 29.2% 1.60% |

Figure 6:
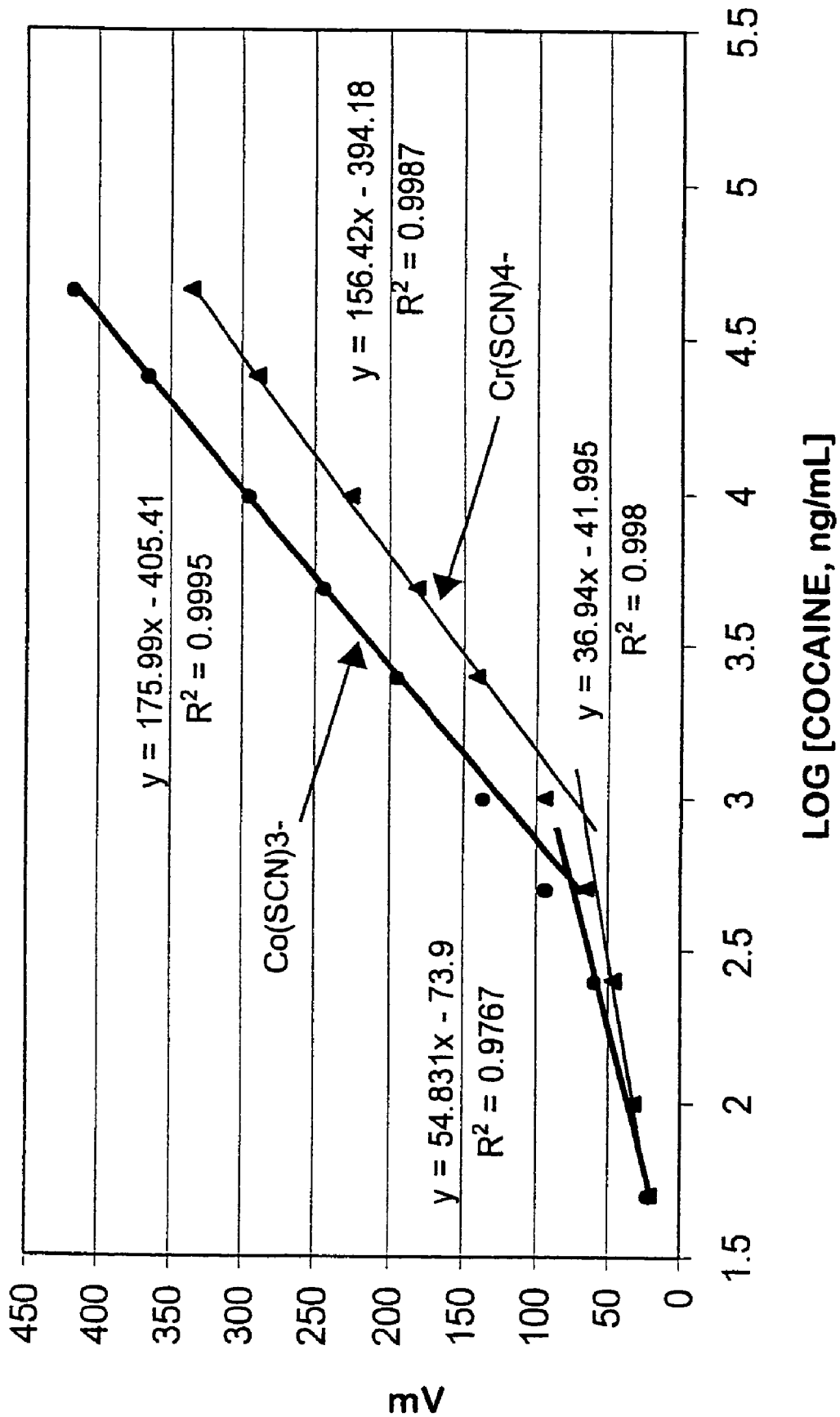
FIG. 6 shows results comparing the cobalt and chromium electrodes from Example 3.

FIG. 6 shows a calibration curve comparison of electrodes made from cocaine cobalt isothiocyanate 1:2 and the cocaine chromium isothiocyanate 1:1 membranes. The sensitivity of the cobalt ionophore response supercede that of the chromium species, the cobalt having a slope 26% greater than the chromium at the higher concentrations and 50% greater at the lower concentrations. The average RSD from the full set of calibrant results are comparable for the two types with 12.3 and 12.9% RSD for the cocaine cobalt isothiocyanate and cocaine chromium isothiocyanate, respectively. Also, the cocaine cobalt isothiocyanate has a lower LOD based on the point of intersection with the x-axis (based on intersection of the Nernstian curve with a horizontal line at the baseline voltage) having a value of 200, while that for the cocaine chromium isothiocyanate is 330 ng/mL. However, in each case the concentration of 50 ng/mL is detectable by using the lower fit of the data.

A direct comparison between wire coated and liquid filled electrodes showed no significant difference in response. However, with liquid filled electrodes, there was a tendency for the membrane to solidify and retract inside the tip of the tubing, leaving a small stagnant region of liquid when placed in a stirred solution. This leads to longer response times on the order of 60 seconds or more for some of the liquid filled electrodes because of transport delays due to diffusion into the unstirred gap. The wire-coated arrays, being planer, did not show this problem.

Example 3

Comparison of Cocaine Cobalt Isothiocyanate to Cocaine Chromium Isothiocyante Carrier Membranes An array of liquid filled cocaine electrodes using 0.1M KCl as the internal filling solution were prepared using a 1:2 cocaine chromium isothiocyanate:Sebacate ratio for three electrodes and a 1:1 cocaine cobalt isothiocyanate:Sebacate ratio for the other three electrodes. The commercial saturate calomel electrode was used as a reference. The buffer was 50 mM sodium acetate, pH 4.5. The calibration curves are shown in FIG. 6 as an average of the three electrodes. The performance advantage of the cocaine cobalt isothiocyanate electrode is clear.

Example 4

Comparison with Cocaine Electrodes Developed by Other Researchers

Figure 7:
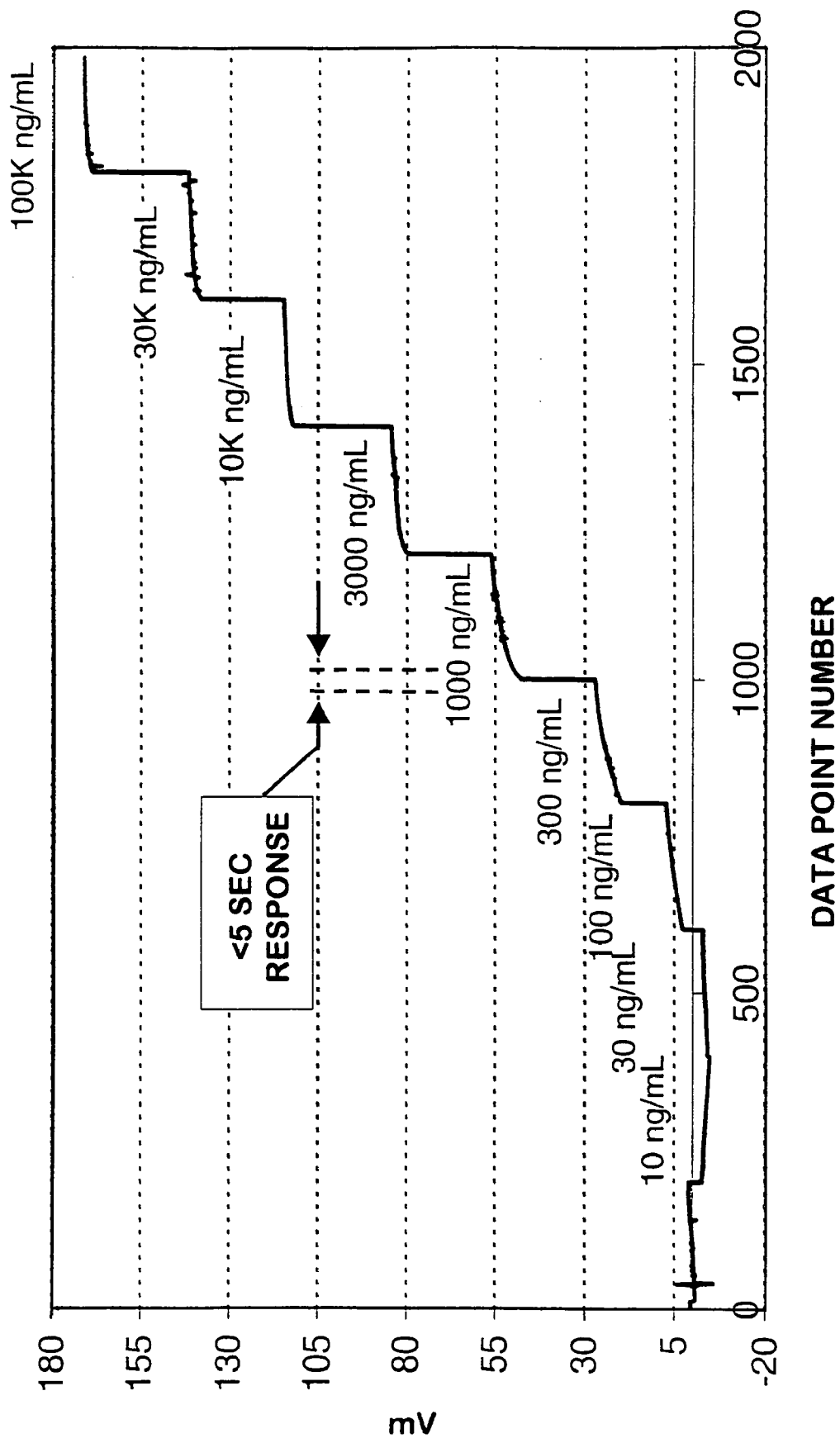
FIG. 7 shows the rapid response of ion selective electrodes to cocaine.

The cocaine electrodes of the present invention show similar characteristics to those developed by others with the added benefit of lower detection limits and faster response times. Table 4 summarizes and compares the cocaine cobalt isothiocyanate electrode preparation (1.1.15 sebacate) with the most sensitive electrodes developed by Elnemma et al., Campanella et al. and Watanabe et al. All of the studies show relatively quick response times and Nernstian behavior with slopes of voltage changes with respect to concentration decades near the theoretical value of 59 mV per decade. As shown in FIG. 7, the present invention typically shows a 5-sec or less response time to achieve 97% of the final response value; however, electrodes with responses in the 30-60 sec time frame (for liquid filled) are sometimes encountered. Part of the response time variation may be a result of differences in membrane thickness (for the wire coated electrodes) or non-planer surfaces (for the liquid filled electrodes, which limits diffusion).

The most notable difference is that the LOD for the present invention is one order of magnitude lower than that reported by Watanabe, and two orders of magnitude lower than the values reported by Elnemma or Campanella. The linear minimum of the present invention is practically two orders of magnitude lower than that reported by Watanabe and Campanella as the Nernstian linear curve for the present invention nearly intersects with the lower curve at 10 ng/mL ($3.3 \times 10^{-8}$ M) and three orders of magnitude lower than reported Elnemma. The lowest detectable level in the non-Nernstian region for the present invention gives a minimum detectable level at 1 ng/mL ($1.4 \times 10^{-8}$ M), which is an order of magnitude lower than a similar value reported by Watanabe. Table 4 lists Elnemma using a potassium based buffer and, though not explicit, it is assumed that the Campanella group used an acetate buffer with a sodium counter ion. The $MgCl_2$ solution used to adjust the ionic strength in the Watanable work was of relatively high concentration, 0.5 M. Because the $Na^+$ cation is shown to be an interferent by the same group, it is possible that this higher concentration prevented the group from achieving the lower detection limits that were observed in this work. Finally, the new cocaine cobalt isothiocyanate complex carrier may account for the improved results.

TABLE 4

Current response characteristics and comparison with literature values.

| Research Group | Electrode/Buffer | Linear Range [mV/log[C]; $R^2$] | Detection Limit [Coc · HCl] | Response Time |
|---|---|---|---|---|
| Elnemma et al. 1992 | Cocaine Tetraphenylborate ISE PVC-dioctyl phthalate 0.1 M Potassium Nitrate pH 3-7.5 | $1 \times 10^{-5}$ to $10^{-2}$ M [54.0 ± 0.4; $R^2$ = 0.999] | $4.5 \times 10^{-6}$ M | 48 s |
| Campanella et al. 1995 | Cocaine$^+$-Cr$^{III}$(-SCN)$_4^-$ (Reineckate) ISFET PVC-Sebacate 0.05 M acetate, pH 5 | $3.3 \times 10^{-6}$ to $2.1 \times 10^{-2}$ [53.9 ± 0.4; no $R^2$] | $\sim 3.3 \times 10^{-6}$ M$^{\dagger\dagger}$ | <25 s |
| Watanabe et al. 1995 | Sodium tetrakis [3,5-bis(trifluoromethyl)phenyl]borate ISE PVC tetrakis(2-ethylhexyl) pyromellitate 0.5 M MgCl$_2$, pH 1-8 | $10^{-6}$ to $10^{-2}$ M [56; no $R^2$] | $4 \times 10^{-7}$ M | <10 s to 90% of final signal |
| (this work) | Cocaine cobalt isothiocyanate ISE Liquid Filled PVC-Sebacate 0.05 M Na acetate, pH 4.5 | $4.1 \times 10^{-6}$ to $1.4 \times 10^{-4}$ M [53.5; $R^2$ = 0.999] $7.8 \times 10^{-8}$ to $4.1 \times 10^{-6}$ M [12.7; $R^2$ = 0.957] | $6.6 \times 10^{-7}$ M $1.1 \times 10^{-7}$ M ($2^{nd}$ curve) | <10 s to 99.9% of final signal |
| (this work) | Cocaine cobalt isothiocyanate PVC-Sebacate ISE Coated Wire 0.05 M Mg acetate, pH 4.5, 0.09 M MgCl$_2$ | $3.3 \times 10^{-8}$ to $2.9 \times 10^{-5}$ M [53.2 ± 0.3; $R^2$ = 0.992] $3.3 \times 10^{-9}$ to $3.3 \times 10^{-8}$ M [4.9 ± 1.4; $R^2$ = 0.793] | $2.7 \times 10^{-8}$ M $1.4 \times 10^{-8}$ M ($2^{nd}$ curve) | Not Studied |

$^{\dagger\dagger}$Campanella et al. reported an approximate value, but with the LOD method defined in this paper, the actual value may be an order of magnitude lower.

Example 5

Analysis of Saliva

Figure 8:
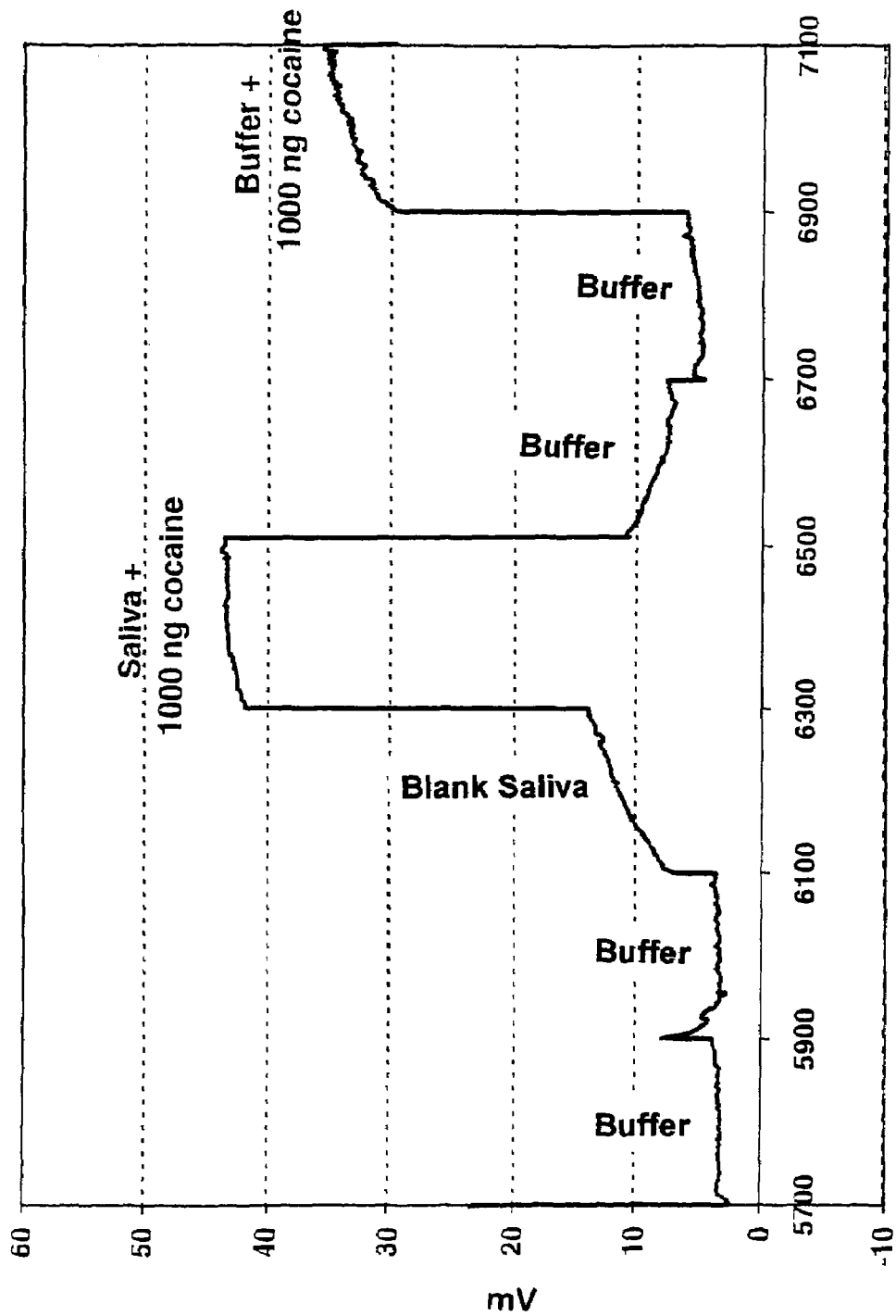
FIG. 8 shows the results of the saliva analysis from Example 5.

Saliva was collected from a drug-free individual using a Sarstedt (Newton, N.C.) number 51.1534.002 saliva collection pad. 100 ul of saliva was placed on an electrode array made of cocaine chromium isothiocyanate:sebacate 1:1 and a cast internal reference electrode. Cocaine was added and a voltage increase was observed. The pH of the saliva was measured to be 5.8 with a conventional pH meter. The results are shown in FIG. 8.

Example 6

Analysis of Surface Wipes

Alcohol swabs were used as a convenient wipe. The alcohol was allowed to evaporate, and the swabs were washed with buffer. The wipes were squeezed, and a glass surface was swabbed with the damp wipe after contamination with known amounts of cocaine. For better quantification, the amount of liquid was controlled. After wiping a surface, the wipes were placed in a vial and buffer was added to a total of 1.2 g of buffer plus wipe. By comparison with dry wipes, this corresponds to ca. 1 mL of buffer. The buffer was squeezed from the wipe and applied to a cocaine sensor array. An average of two trials is presented in Table 5 and FIG. 9.

TABLE 5

Summary of surface wipe analysis results

| [Cocaine] placed on glass surface | 500 ng | 1500 ng | 5000 ng | 15000 ng |
|---|---|---|---|---|
| Membrane #1 [Cocaine] measured | 210 | 910 | 1320 | 3300 |
| Membrane #2 [Cocaine] measured | 470 | 2300 | 3600 | 12500 |
| Membrane #3 [Cocaine] measured | 570 | 2250 | 3500 | 13400 |
| Membrane #4 [Cocaine] measured | 620 | 2200 | 3300 | 12400 |
| Membrane #5 [Cocaine] measured | 560 | 3100 | 5300 | 16500 |
| Membrane #6 [Cocaine] measured | 350 | 1860 | 3300 | 11000 |

The above description is that of a preferred embodiment of the invention. Various modifications and variations are possible in light of the above teachings. It is therefore to be understood that, within the scope of the appended claims, the invention may be practiced otherwise than as specifically described. Any reference to claim elements in the singular, e.g. using the articles "a," "an," "the," or "said" is not construed as limiting the element to the singular.

The invention claimed is:

1. A method of making a cast membrane reference electrode comprising the steps of:
    (a) casting a membrane over a hole wherein said membrane is comprised of a hydrophilic polymer and a hydrophobic polymer;
    (b) filling the interior of the hole with a solution;
    (c) placing a wire into the solution; and
    (d) sealing the hole;
    wherein the cast membrane reference electrode results in a half-cell where the reference voltage is substantially independent of the concentration of ionic species in solution;
    and
    wherein said hydrophobic polymer is polyvinyl chloride.
2. The method of claim 1 wherein said hydrophilic polymer is polyethylene glycol, polyethylene glycol grafted onto a hydrophobic molecule, polypropylene glycol, or polypropylene glycol grafted onto a hydrophobic molecule.

3. A cast membrane reference electrode comprising:
(a) a support containing a hole;
(b) a membrane cast over the hole in the support wherein said membrane is comprised of a hydrophilic polymer and a hydrophobic polymer;
(c) a solution in the interior of the hole in the support; and
(d) a wire in the solution;
wherein the cast membrane reference electrode results in a half-cell where the reference voltage is substantially independent of the concentration of ionic species in solution; and
wherein said hydrophobic polymer is polyvinyl chloride.

4. The cast membrane reference electrode of claim 3 wherein said hydrophilic polymer is polyethylene glycol, polyethylene glycol grafted onto a hydrophobic molecule, polypropylene glycol, or polypropylene glycol grafted onto a hydrophobic molecule.

* * * * *

UNITED STATES PATENT AND TRADEMARK OFFICE
CERTIFICATE OF CORRECTION

| | | |
|---|---|---|
| PATENT NO. | : 7,618,523 B2 | Page 1 of 1 |
| APPLICATION NO. | : 10/833636 | |
| DATED | : November 17, 2009 | |
| INVENTOR(S) | : David A. Kidwell | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1578 days.

Signed and Sealed this

Twenty-sixth Day of October, 2010

David J. Kappos
*Director of the United States Patent and Trademark Office*